United States Patent
Hilton et al.

(10) Patent No.: US 10,456,299 B2
(45) Date of Patent: Oct. 29, 2019

(54) GOGGLES WITH INTERCHANGEABLE LENS ATTACHMENT

(71) Applicant: Maui Jim, Inc., Peoria, IL (US)

(72) Inventors: Molly McCall Hilton, Boulder, CO (US); Benjamin Russell Peters, Lafayette, CO (US); Pengfei Li, Qingdao (CN); Libao Xu, Chengyang (CN); Michael Patrick Croke, Incline Village, NV (US); Daniel Scot Barone, Morrison, CO (US); Michael Thomas Lewis, Boulder, CO (US)

(73) Assignee: Maui Jim, Inc., Peoria, IL (US)

( * ) Notice: Subject to any disclaimer, the term of this patent is extended or adjusted under 35 U.S.C. 154(b) by 335 days.

(21) Appl. No.: 15/380,159

(22) Filed: Dec. 15, 2016

(65) Prior Publication Data

US 2018/0168865 A1 Jun. 21, 2018

(51) Int. Cl.
  *A61F 9/02* (2006.01)
(52) U.S. Cl.
  CPC .................................. *A61F 9/025* (2013.01)
(58) Field of Classification Search
  CPC ........................................................ A61F 9/025
  See application file for complete search history.

(56) References Cited

U.S. PATENT DOCUMENTS

| | | | |
|---|---|---|---|
| 6,964,067 B1 | 11/2005 | Hartman | |
| 7,058,991 B2 | 6/2006 | Hartman et al. | |
| 2009/0079930 A1 | 3/2009 | Lipawsky | |
| 2009/0222979 A1* | 9/2009 | Wang | A61F 9/025 2/431 |
| 2013/0091623 A1 | 4/2013 | McCulloch et al. | |
| 2013/0185849 A1* | 7/2013 | Laughlin | A61F 9/025 2/431 |
| 2016/0143784 A2 | 5/2016 | Arnette | |

OTHER PUBLICATIONS

Burton / Men / anon. / Goggles & Lenses: anon. M2 Goggle, obtained from the internet https://www.burton.com, and images of Goggles, Dec. 6, 2016, 23 pages.
Oakley Airbrake Snow in JET Black / Fire Iridium / Oakley, obtained from the internet http://www.oakley.com, and images of Goggles, Dec. 6, 2018, 26 pages.

* cited by examiner

*Primary Examiner* — Anna K Kinsaul
(74) *Attorney, Agent, or Firm* — Brinks Gilson & Lione

(57) ABSTRACT

A goggles system includes an inner frame dimensioned and contoured for positioning against a wearer's face with a plurality of interchangeable lens assemblies, where each lens assembly is removably attachable to the inner frame by an engagement mechanism that includes at least one tongue and groove attachment and at least one magnetic attachment. The lens(es) of each interchangeable lens assembly may be the same as or different from each other.

20 Claims, 7 Drawing Sheets

GOGGLES WITH INTERCHANGEABLE LENS ATTACHMENT

TECHNICAL FIELD

Embodiments disclosed herein generally relate to goggles. More particularly, disclosed embodiments of goggles systems include a connection mechanism for ready installment and removal of interchangeable lenses (e.g., allowing for variability/adaptability to different lighting, weather, and other goggle-affecting conditions).

BACKGROUND

Eye-protecting sports goggles are used in a variety of sports and activities including skiing, snowboarding, cycling, skydiving, paintball, ATV/snowmobile/motorcycle-riding, and many more. Different lighting and environmental conditions can present a variety of different challenges for which a single pair of goggles is not universally well-suited. Conventional goggles typically include a plastic and/or metallic body with a lens or pair of lenses mounted therein in a manner and position away from a wearer's eyes, but with the frame providing a border around a periphery between the lens(es) and the wearer's face. The rear/wearer-facing side often includes soft, compliant, or otherwise conforming material to provide for wearer comfort and a seal or at least form-fitting relationship between the goggles and the wearer's face. Most conventional goggles also include a strap or other structure for holding the goggles in place on a wearer's face, which may attach to and/or fit around the wearer's head, helmet, and/or other headgear.

Most goggles do not have interchangeable lenses, and particularly interchangeable lenses that may be swapped easily without sacrificing the security and functionality of assembled goggles. Therefore, it may be desirable to provide goggles with a mechanism for easy removal and replacement of a lens assembly by a wearer.

BRIEF SUMMARY

The present system will allow a wearer to changes lenses without removing his/her goggles (at least the strap and base/inner frame portion), for example, to deal with different lighting conditions, to replace lenses that are dirty for later cleaning, to provide a different look/color/finish, or any other purpose for which same, similar, or different lenses might be desired without replacing the entire pair of goggles. Those of skill in the art will appreciate that various lens assemblies including different lens members and sub-elements thereof may readily be used within the present goggles system if configured with the attachment/removal system described herein.

In one aspect, embodiments disclosed herein may include a goggles system with an inner frame dimensioned and contoured for positioning against a wearer's face with a plurality of interchangeable lens assemblies, where each lens assembly is removably attachable to the inner frame by an engagement mechanism that includes at least one tongue and groove attachment and at least one magnetic attachment. The lens(es) of each interchangeably lens assembly may be the same as or different from each other. Individual goggles may include one or more removable/interchangeable lens assemblies that fit well with and attach securely to an inner frame.

Figure 8:
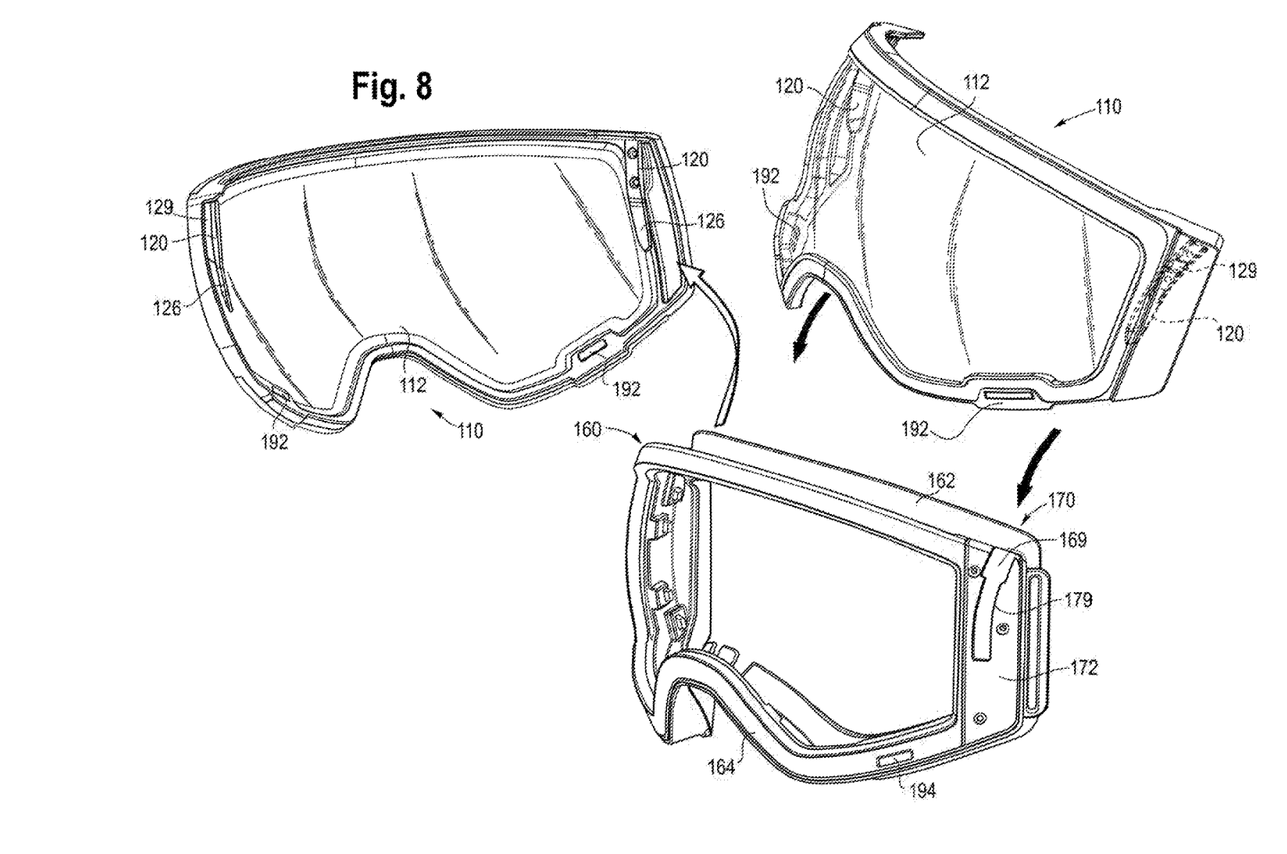
FIG. 8 shows a goggles system with an inner frame and two lens assemblies.

In one aspect, embodiments disclosed herein may include goggles with an inner frame dimensioned and contoured for positioning against a wearer's face, which inner frame includes at least a first one of a flange-edged tongue or a tongue-receiving groove; and a plurality of interchangeable lens assemblies, wherein: each lens assembly is removably attachable to the inner frame by an engagement mechanism that includes the other of a flange-edged tongue or a tongue-receiving groove, configured to removably engage with the at least first one of a flange-edged tongue or a tongue-receiving groove, and at least one magnetic attachment structure that corresponds to a magnetically-complementary structure of the inner frame; each lens assembly includes a major curve between left and right ends thereof, with an intermediate portion of said curve being nearer a front than a rear of the lens assembly; and each of the flange-edged tongue and tongue-receiving groove is complementarily curved along its longitudinal axis, which longitudinal axis is nearer (to alignment with) an axis between top and bottom borders of the goggles system than a front-rear axis of the goggles system (shown at least in FIG. 8).

DETAILED DESCRIPTION

Various embodiments provide goggles and a goggles system meeting the need for goggles with interchangeable lenses, which embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale (although drawings may be to scale, and may be relied upon as such for purposes of defining claim limitations), and in certain instances details may have been omitted that are not necessary for an understanding of embodiments disclosed herein, such as—for example—conventional fabrication and assembly. The state of the art for sports goggles is many decades old and very well developed, such that those of skill in the art will appreciate that the connection mechanism embodiments and connection system embodiments described herein may readily be implemented in goggles using otherwise standard components (e.g., materials used to construct lens frames, lenses, inner/face frames, and other goggle components). In view of the teaching presented here, those of skill in the art will be enabled to implement the attachment structures described below in different sport goggles.

Generally, engagement mechanisms including attachment structures for a goggles system with interchangeable lens assemblies will include one or a plurality of lens assemblies and an inner frame configured (dimensioned and contoured for) positioning on/against a wearer's face over the wearer/user's eyes in the manner of typical goggles. Each lens assembly will be slidably movably engageable with the inner frame. The engagement will include at least one tongue and groove engagement, and at least one magnetic engagement. The tongue will be on one of the lens assembly or the inner frame, with a complementary groove dimensioned and contoured for engagingly receiving the tongue on the other of the inner frame or the lens assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein.

The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to an engineer or other eyewear/goggles designer with experience in this field), and should be interpreted to include at least any legal equivalents, minor but functionally-insignificant variants, standard manufacturing tolerances, and including at least mathematically significant figures (although not required to be as broad as the largest range of significant figures). The term "interengage" (and any variants thereof) are used to describe and define a mating relationship that includes overlap in multiple planes (e.g., interlocking J's; mortice/tenon with flare of dovetail or T-section); within the present disclosure, interengaging tongue-and-groove structures are disclosed and may be considered as preferred, but a non-interengaging tab-slot arrangement may be used as well, and may be within the scope of claimed subject matter unless excluded.

One embodiment of a goggles device is described with reference to FIGS. 1-8C, which show views of a goggles device and system including a removable lens assembly 110 (shown in FIG. 1 as a plurality of lens assemblies 110, the left one of which is shown assembled, and the right one of which is partially-exploded) and an inner frame member 160. Certain standard goggles components including, for example, straps, vents, and other elements may not be shown and/or may not be identified by reference number, but will be understood and appreciated by those of skill in the art to be part of different goggles for different sport applications, but not essential to understanding the present attachment mechanisms.

Figure 1:
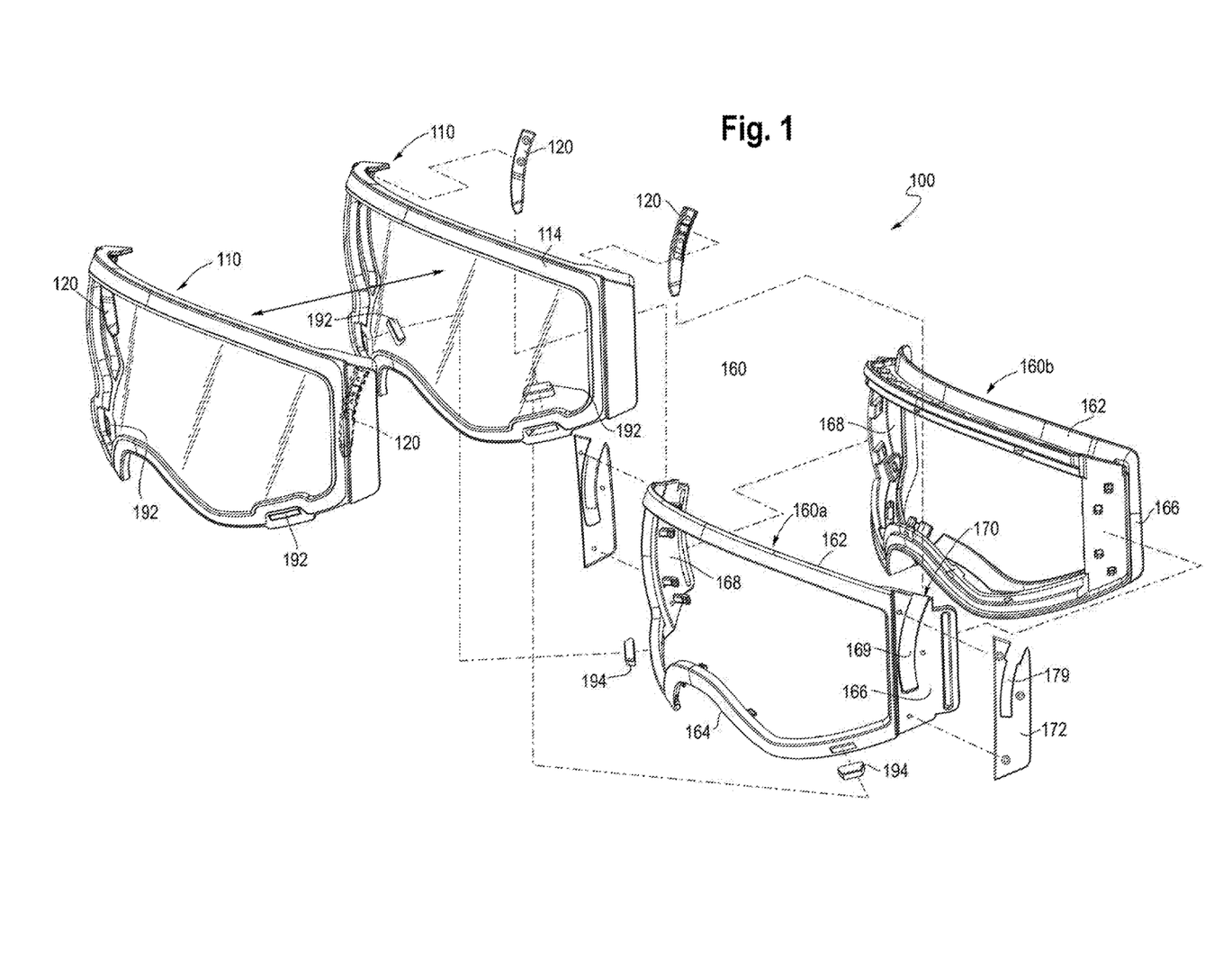
FIG. 1 shows a partially exploded views of goggles and a goggles system.

A goggles system 100 is shown in a partially-exploded view in FIG. 1, where the system includes a plurality of lens assemblies. Each lens assembly 110 includes a lens member 112 (with one example shown in greater detail in FIG. 2). The lens assembly is formed and sized to extend across eyes of the wearer to cover the eyes and eye-adjacent area of the wearer. The lens may be configured having a curved, arcuate shape across its longest axis (left-right); for embodiments where this is the only significant lens curvature, the lens is known in the art as "cylindrical." Different lens embodiments may also have a curved arcuate shape across the shorter axis (top-bottom), known in the art as "spherical lenses." The lens member 112 (which may otherwise be embodied as a pair of lenses separated in the middle/nose portion by a divider, not shown but known in the art), is circumferentially encompassed by a bordering lens frame 114.

Figure 2:
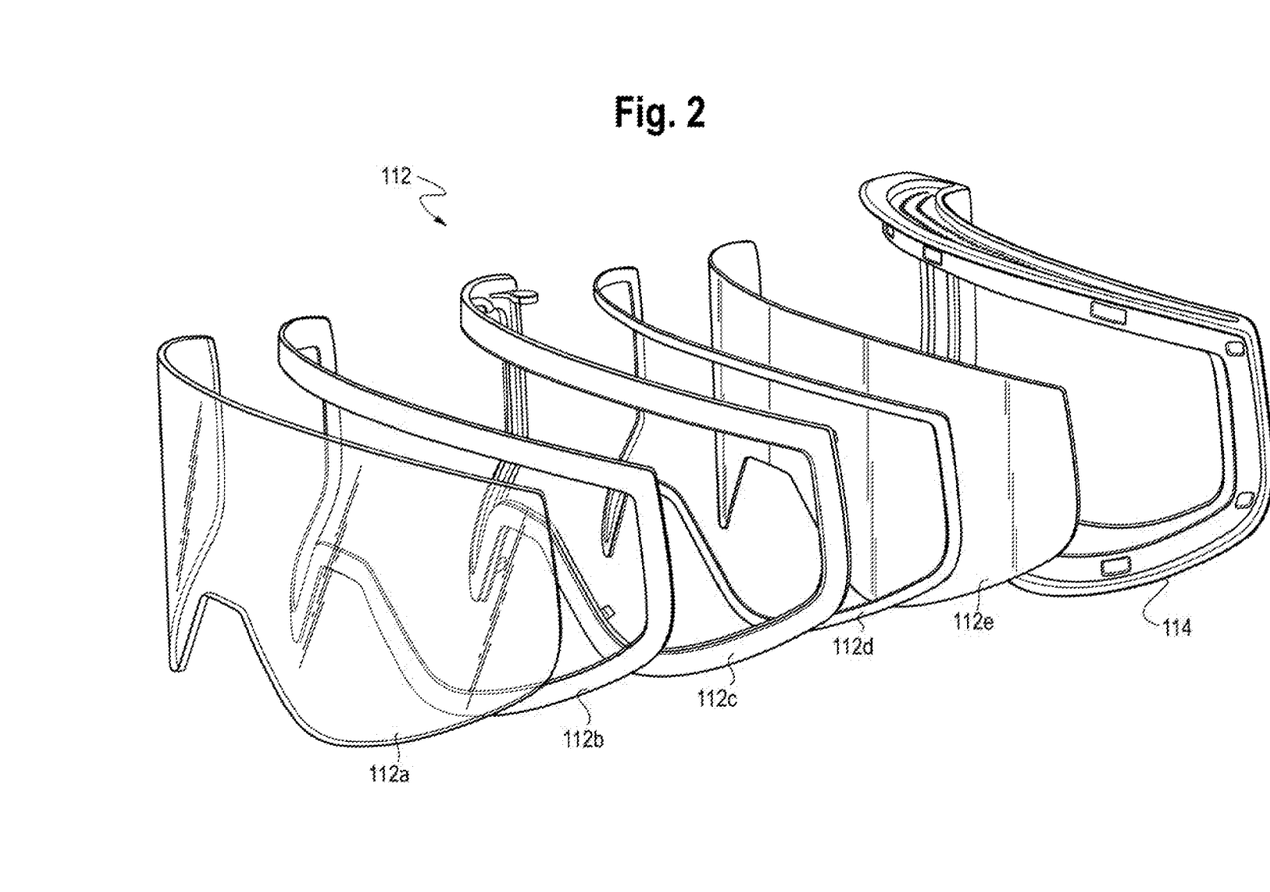
FIG. 2 is a partially exploded view of a lens assembly embodiment.

As shown in one non-limiting example illustrated in FIG. 2, a lens member 112 may include a plurality of components including in the illustrated embodiment an outer lens 112a, an outer gasket or tape border 112b, a lens rim 112c, an inner gasket or tape border 112d, and an inner lens 112e. In a system like that shown in FIG. 1, interchangeable lens assemblies each may have same, similar, or different lens members 112.

The lens frame 114 is configured so that it matches up against and/or mates with the inner frame 160. In the embodiment shown in FIG. 1, the inner frame includes a front frame element 160a and a rear frame element 160b; however, those elements may be formed together in other embodiments, and—unless otherwise specified—the inner frame 160 is addressed herein as a single component (whether formed as an integrated monolithic unit or as the front and rear elements 160a, 160b, where the present disclosure including those describing the following portions of the inner frame may be read to include those elements 160a, 160b together as a unit). The inner frame 160 includes a top (forehead) cross-piece 162, and a bottom (cheek/nose) cross-piece 164 that join a left end member 166 and a right end member 168, each of which extend generally vertically between the cross-pieces. The cross-pieces each preferably are curved or otherwise contoured to fit a wearer's face in any of the configurations already known, or yet-to-be developed. The cross-pieces 162, 164 and end members 166, 168 each may include a plurality of components, or may be formed integrally as a monolithic inner frame (up to and including those elements being integrally formed, for example, by molding or other means).

Rear-facing surfaces of the lens frame 114 preferably are configured to complementarily mate with or otherwise fit against the front-facing surfaces of the inner frame 160, and the left/right inward-facing end members of the lens frame preferably are configured to complementarily mate with or otherwise fit against the outward-facing left/right surfaces of the inner frame 160. Each lens assembly includes a major curve between left and right ends thereof and may include a minor curve between top and bottom borders thereof, with an intermediate portion of said major curve and said minor curve each being nearer a front than a rear of the lens assembly, although the minor curve may be negligible or even absent in certain embodiments (e.g., "cylindrical" lens embodiments).

The goggles 100 include complementary inward-facing attachment structures and outward-facing attachment structures for slidably removably engaging each lens assembly 110 with the inner frame 160, where each of those components comprises one or more attachment structures that is complementary to/with an attachment structure on the other component. As shown in FIG. 1, with further reference to the subcomponent and component views of FIGS. 3-8C, the attachment structures may include one or both of a tongue-and-groove attachment and a magnetic attachment. When engaged, the attachment structures, each of which includes a first element on one of the inner frame 160 or the lens assembly 110, with a second element—complementary to the first element—on the other of the inner frame 160 or the lens assembly 110.

Figure 3A:
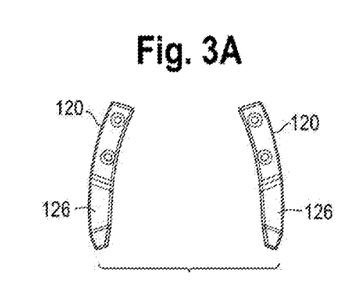
FIGS. 3A-3C show views of a tongue member.
Figure 3B:
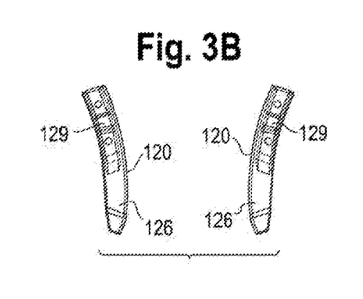
Figure 3C:
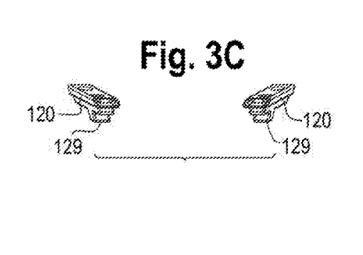

In the embodiments illustrated herein, the lens assembly 110 includes a pair of tongue members 120, and the inner frame 160 includes a pair of grooves 170 configured (that is, dimensioned and shaped) to slidably and releasably receive the tongue member 120. The tongue members 120 are shown enlarged in the views of FIGS. 3A-3C and 8A. FIGS. 3A, 3B, and 3C show, respectively, the inward-facing sides, the outward-facing sides, and a partially-perspective top-end-on view of the tongue members 120. As shown in FIG. 1, with reference also to the enlarged views of FIGS. 4A-4C and 8A-8C, the grooves 170 are formed by groove housings 172 and groove channels 169 on the end-facing surfaces of the end members 166, 168 of the inner frame 160.

Figure 7:
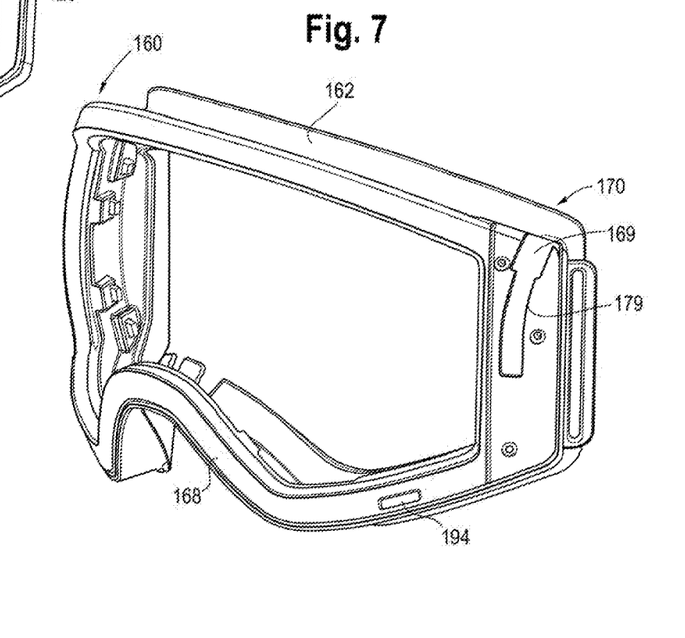
FIG. 7 is a front perspective view of an inner frame member.
Figure 8A:
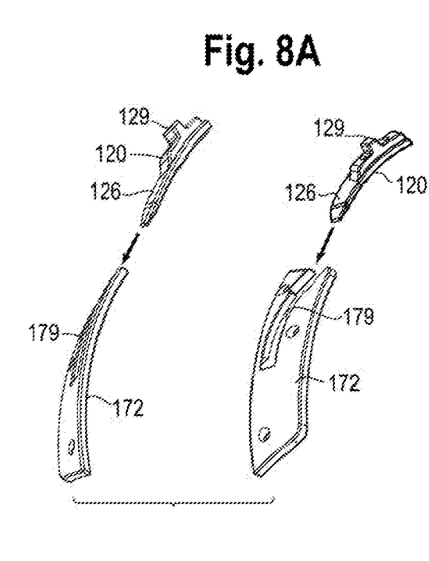
FIGS. 8A-8C show disengaged and engaged views of tongue-and-groove members of the goggles system.
Figure 8B:
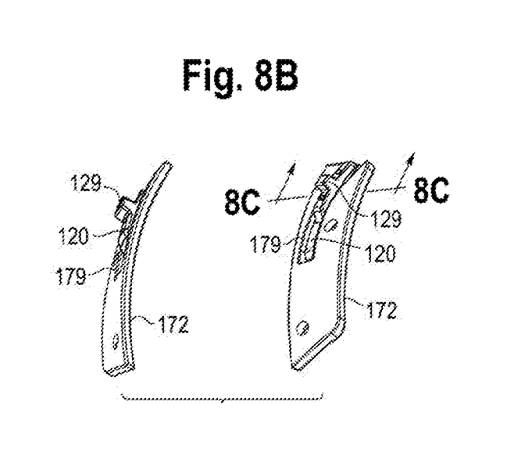
Figure 8C:
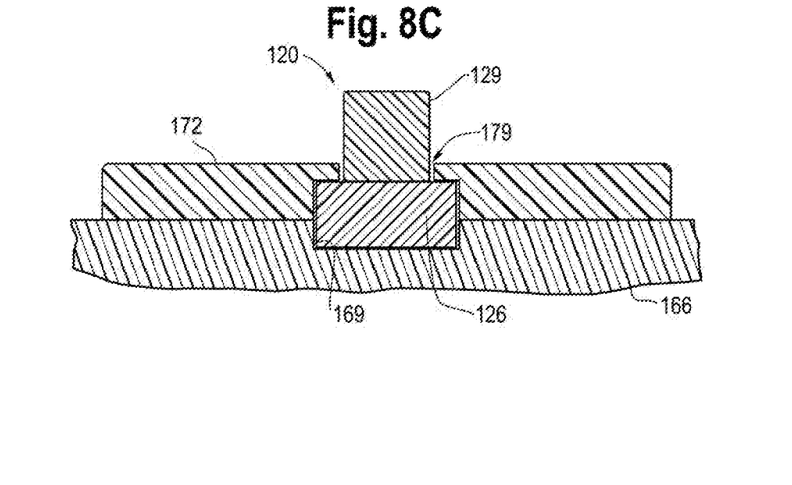

In the embodiments show, at least a portion of the tongue members 120 includes a solid T-shaped transverse cross-section as shown in the perspective end-on view of FIG. 3C (and also in FIG. 8C, which is drawn magnified), where some embodiments may also include an asymmetrical T-shape in longitudinal section (e.g., see FIGS. 3C and 8A-8B). As should be understood from the drawings (especially FIGS. 1, 7, and 8-8C), at least a portion of the outward facing attachment structure includes a groove 169, 179 with T-shaped transverse cross-section dimensioned to receive, engage, and release the tongue members 120. Whether or not the tongue or groove includes a T-shaped cross-section, preferred embodiments will engagingly fit together, which may include the tongue having one or more longitudinal-edge flanges with a corresponding receiving region of the complementary/receiving groove. FIG. 8B shows a transverse section view of a tongue member 120, inserted into the groove 169, 179, where the section view is taken along line 8C-8C of FIG. 8B, and also includes the inner groove portion 169 formed on the outer face of the inner frame 160. In the illustrated embodiment, the tongue member includes a neck 129 and a flanged or otherwise wider-than-the-neck tongue member body 126. In FIG. 8C, the illustrated embodiment includes a T-shaped transverse section, but it will be appreciated that this section view could be L-shaped or any other geometry that will provide for interengagement with the groove 170, as shown in FIG. 8B. In the illustrated embodiments, the neck 129 is extends longitudinally along, but less than the full length of, the tongue body 126, but the exact proportion of that may vary in other embodiments.

Figure 4A:
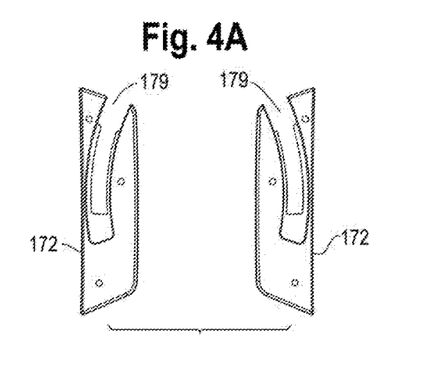
FIGS. 4A-4C show views of a groove housing member.
Figure 4B:
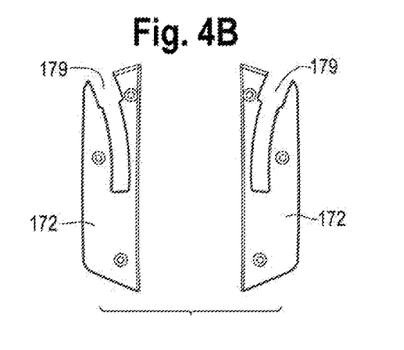
Figure 4C:
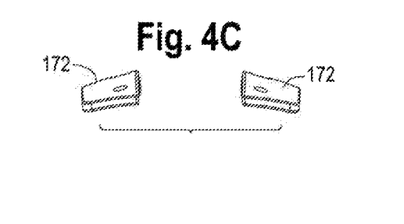
Figure 6:
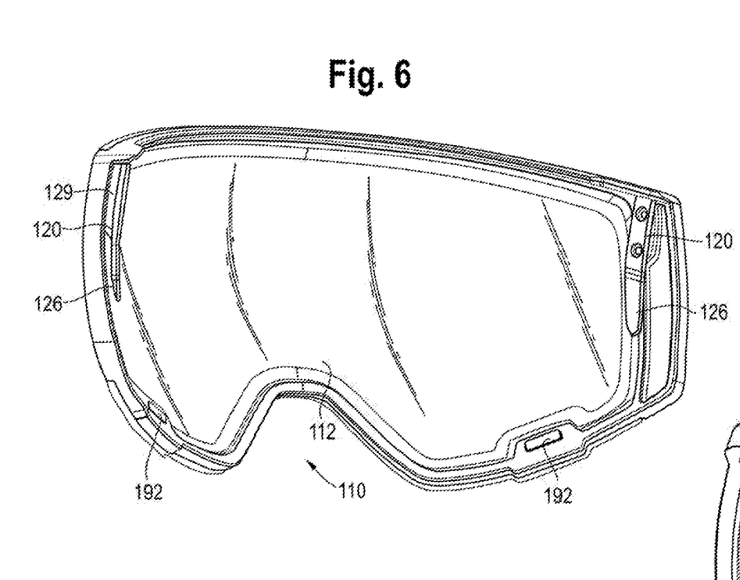
FIG. 6 is a rear perspective view of a lens assembly.

FIGS. 4A, 4B, and 4C show, respectively, the inward-facing sides, the outward facing sides, and a bottom-end-on view of the groove housings 172, while FIG. 8A shows a perspective view of the groove housings 172. FIG. 6 shows a rear perspective view of the lens assembly 110, including the tongue members 120, and FIG. 7 shows a front perspective view of the inner frame 160, including the groove 170. The groove housings 172 each include a slot 179 that receives the neck 129 of a complementary tongue member 120 as the flanged or otherwise wider-than-the-neck tongue member body 126 is received into the groove 170 formed by the slot 179, groove housing 172, and groove channel 169. Of course, those of skill in the art will appreciate that the components of interengaging or non-interengaging tongue and groove structures may each be molded as a single component or otherwise constructed within the scope of the present disclosure.

The tongue members 120 and the grooves 170 are illustrated as complementarily curved along their respective longitudinal axes. A major top-to-bottom curve of each may parallel or otherwise be proportional to a top-to-bottom curvature of the lens assemblies 110, bowing toward the front with ends nearer the rear. A minor curve of the tongue and groove may include bowing out toward the right for the right-side tongue member 120 (as shown in FIG. 6) and out toward the left for the left-side tongue member 120. Any curvature(s) of the grooves 160 will complement the curvature(s) of the tongue members 120, although radii of curvature may vary somewhat from each other (e.g., by way of providing workable tolerances, intentionally providing for frictional engagement between the tongue and groove as they become fully engaged). The leading, lateral, and/or trailing edges of the body 126 of the tongue members 120 may be rounded, chamfered, and/or tapered whether in the manner illustrated or otherwise.

Figure 5:
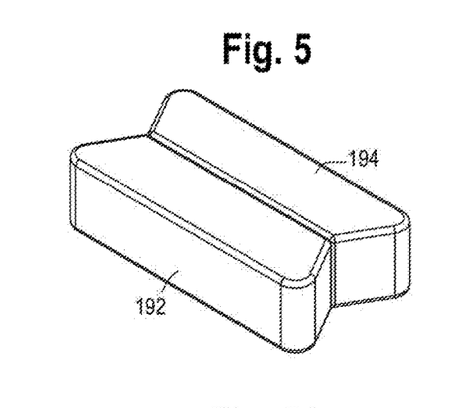
FIGS. 5-5D show views of a magnetic connector elements.
Figure 5A:
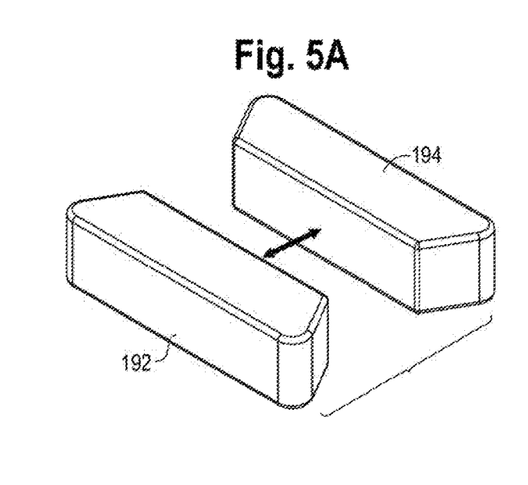
Figure 5B:
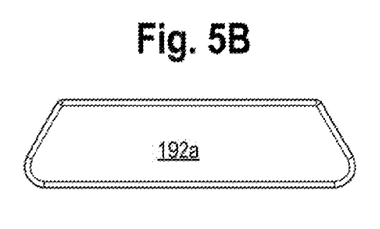
Figure 5C:
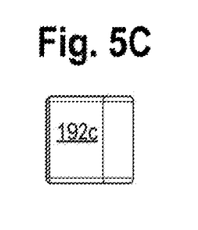
Figure 5D:
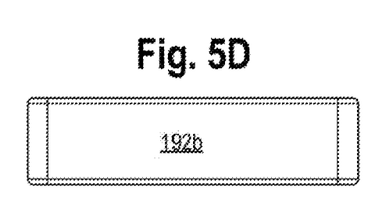

For the goggles 100, at least one of the attachment structures preferably includes at least one magnetically-complementing pair including at least a first magnet and/or a first ferromagnetic mass 192 with a magnetically-complementary second magnet and/or a second ferromagnetic mass 194. FIG. 5 shows one example of a magnetically-connected pair 192/194, and FIG. 5A shows connection/disconnection between the pair, while FIGS. 5B, 5C, and 5D respectively show lateral side face 192a, non-connecting face 192b, and end face 192c of one exemplary embodiment. The embodiment shown includes a generally trapezoidal cross section in at least one dimension, where the illustrated embodiment approximates a round-cornered/round-edged three-dimensional trapezoid, but other geometries could readily be used. Preferred magnets may include rare earth magnets or other strong magnets, and/or they may include weaker (e.g., ferrite, alnico) magnets. The term ferromagnetic mass is used to refer to a metallic or other material to which a magnet will be drawn and attach with sufficient strength to resist displacement.

In the goggles described here, the magnetic attachments are located along the lower rims of the lens assembly 110 and the inner frame 160, where they can serve to secure the lens assembly in place together with the tongue and groove or other mechanically interengaging connection (where the term "interengaging" refers to a mechanical engagement where both elements overlap each other and thereby allow for movement along respective longitudinal axes, but to resist or even prevent separation by moving those respective longitudinal axes away from each other). Each magnetically complementary pair may include two magnets mounted for mutual attraction/attachment (i.e., where opposite poles will contact or nearly contact), or one magnet and one ferromagnetic mass mounted for attraction/attachment together.

For example, as illustrated with reference to FIG. 1 and FIGS. 6-7, a magnet 192 may be mounted in or on the lower rim/cross-piece of the lens assembly 110, and another magnet 194 (or ferromagnetic mass) may be mounted in or on the front-facing lower cross-piece 164. If both are embodied as magnets, then the opposing poles will be oriented to connect them magnetically when placed in proximity (e.g., as shown in FIG. 5). In these illustrations, the matching magnet+magnet or magnet+ferromagnetic mass (in either orientation, with one in the lens assembly 110 and the other in the inner frame 160, or vice versa) are shown below the space that will be in front of a wearer's left eye. However, as shown elsewhere in the drawings and as will be appreciated, another magnetic connector may be mounted in a symmetrically disposed or otherwise disposed position—e.g., below the right eye, over the nose bridge, any other position(s) around the respective rims, and/or any combination thereof, including on the left and/or right ends adjacent to or included with the tongue and groove connecting structures. With the three-dimensional trapezoidal geometry shown for the magnets/masses 192/194, one preferred orientation will be to have the broader base secured in the goggles component and the narrower top side be the contact surface with the respective magnetic complement, but those of skill in the art will appreciate that other shapes and geometries can be used in view of the present disclosure.

In view of the embodiments described and illustrated here, it will be appreciated that engagement of the lens assembly with the inner frame describes a top-toward-bottom arced path, and disengagement of the lens assembly from the inner frame describes a bottom-toward-top arced path. FIG. 8 shows a removed first lens assembly 110 on the left side, and also shows that a second lens assembly 110 can be mounted into the inner frame 160 by engaging the tongue-and-groove elements fully until the lens assembly magnetic elements 192 align with and engage the inner frame magnetic elements 194. In this manner for the illustrated embodiment (e.g., with reference to FIGS. 8A-8C), the tongue members 120 will be fed into the grooves 170, and the lens assembly 110 will be slid/arced downward to fully engage the tongue members 120 into the grooves 170. At the time and position when that engagement is complete or nearly complete, the magnets/masses 192/194 will be complementarily aligned and help secure the lens assembly in place. A click-lock detent engagement, frictional engagement, and/or other engagement(s) between the tongue and groove elements and/or other elements may further securely but removably attach the lens assembly 110 to the inner frame 160. The described features may include being configured wherein an action of engaging the inward-facing attachment structures of the lens assembly 110 with corresponding outward-facing attachment structures of the inner frame 160 provides tactile and/or audible indicia of engagement and/or disengagement to a wearer (e.g., a "click" or "snap" noise as the tongue/groove and/or magnetic connection elements fully engage, or visual indicia such as a pop-button, color change, light/LED activation, etc.). For example, a wearer may (with the goggles inner frame being worn, or being held) remove a lens assembly by arcing it upward and rearward and then mount the same or a different lens assembly by reversing the motion—arcing it downward and forward relative to the inner frame.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. This expressly includes that each of the different tongue-and-groove attachment structures and the different magnetic attachment structures can be mixed and matched so as to be used in any combination with each other. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A goggles device including a removable lens assembly, the goggles device comprising:
   an inner frame dimensioned and contoured for positioning against a wearer's face; and
   a first lens assembly including:
   a first lens formed and sized to extend across eyes of the wearer to cover the eyes and eye-adjacent area of the wearer, said lens having an arcuate shape across at least its longest axis; and
   a plurality of inward-facing attachment structures of the lens assembly dimensioned to engage with corresponding outward-facing attachment structures of the inner frame,
   wherein at least one of the plurality of inward-facing attachment structures is curved along its longitudinal axis and slidably removably engages with a complementarily curved at least one of the outward-facing attachment structures of the inner frame; and
   configured such that engagement of the lens assembly with the inner frame describes a top-toward-bottom arced path, and disengagement of the lens assembly from the inner frame describes a bottom-toward-top arced path, said arced path being defined by the curved longitudinal axis of the at least one of the plurality of inward-facing attachment structures, the complementary curvature of the at least one of the outward-facing attachment structures of the inner frame, or both the curved longitudinal axis and the complementary curvature.

2. The goggles device of claim 1, where the plurality of inward-facing attachment structures of the lens assembly includes a pair of tongue members, with one tongue member disposed near each of a right end and a left end of the lens assembly.

3. The goggles device of claim 2, where each of a pair of the outward-facing attachment structures of the inner frame is complementary to one of the pair of tongue members—including being dimensioned to slidably receive, engage, and release the tongue members—and where a first of the pair of outward-facing attachment structures faces more toward a right end of the goggles device than toward a front of the of the goggles device, and a second of the pair of outward-facing attachment structures faces more toward a left end of the goggles device than toward a front of the goggles device.

4. A goggles device including a removable lens assembly, the goggles device comprising:
   an inner frame dimensioned and contoured for positioning against a wearer's face; and
   a first lens assembly including:
   a first lens formed and sized to extend across eyes of the wearer to cover the eyes and eye-adjacent area of the wearer, said lens having an arcuate shape across at least its longest axis; and
   a plurality of inward-facing attachment structures of the lens assembly dimensioned to engage with corresponding outward-facing attachment structures of the inner frame,
   wherein at least one of the plurality of inward-facing attachment structures is curved along its longitudinal axis and slidably removably engages with a complementarily curved at least one of the outward-facing attachment structures of the inner frame;

where the plurality of inward-facing attachment structures of the lens assembly includes a pair of tongue members, with one tongue member disposed near each of a right end and a left end of the lens assembly;
where at least a portion of the tongue members includes a solid T-shaped transverse cross-section, and at least a portion of a complementary outward facing attachment structure includes a groove with T-shaped transverse cross-section dimensioned to receive, engage, and release the tongue members.

5. The goggles device of claim 4, where each of the grooves is open at its top end, such that a longitudinal end of each tongue can enter and slide into the open top end of each groove.

6. The goggles device of claim 5, configured such that engagement of the lens assembly with the inner frame describes a top-toward-bottom arced path, and disengagement of the lens assembly from the inner frame describes a bottom-toward-top arced path.

7. The googles device of claim 1, wherein
the plurality of inward-facing attachment structures of the lens assembly comprises at least one magnetically-complementing pair including at least a first magnet, a first ferromagnetic mass, or both a first magnet and a first ferromagnetic mass; and
at least one of the outward-facing attachment structures includes at least a second magnet, a second ferromagnetic mass, or both a second magnet and a second ferromagnetic mass,
where the at least a second magnet, a second ferromagnetic mass, or both a second magnet and a second ferromagnetic mass, aligns with and magnetically attaches to the at least a first magnet a first ferromagnetic mass, or both a first magnet and a first ferromagnetic mass when another of the plurality of inward-facing attachment structures of the lens assembly is engaged with a complementary one of the outward-facing attachment structures, wherein at least one member of each magnetically-complementing pair comprises a magnet.

8. The goggles device of claim 1, comprising a plurality of complementary magnetic connectors, each of the complementary magnetic connectors including a first portion comprised by the lens assembly and a second portion comprised by the inner frame.

9. The goggles device of claim 8, where at least one magnet of the plurality of complementary magnetic connectors comprises a generally trapezoidal cross section in at least one dimension.

10. The goggles device of claim 8, where at least one of the plurality of complementary magnetic connectors is comprised along a lower rim of the first lens assembly and a corresponding lower rim of the inner frame.

11. The goggles device of claim 1, configured wherein an action of engaging the inward-facing attachment structures of the lens assembly with a corresponding outward-facing attachment structures of the inner frame provides to a wearer:
tactile indicia, audible indicia, or both tactile and audible indicia of engagement,
tactile indicia, audible indicia, or both tactile and audible indicia of disengagement, or
tactile indicia, audible indicia, or both tactile and audible indicia of both engagement and disengagement.

12. The goggles device of claim 1, wherein two of the plurality of inward-facing attachment structures of the lens assembly are configured as tongue members, each tongue member flanged along at least one longitudinal edge, and a corresponding two of the outward-facing attachment structures of the inner frame are configured as grooves that fittingly receive and frictionally engage around flanges of the tongue members.

13. A goggles system comprising:
an inner frame dimensioned and contoured for positioning against a wearer's face, said inner frame being longer across a left-right width than it is tall from a top boundary to a bottom boundary height; and
a plurality of interchangeable lens assemblies, where each lens assembly is removably attachable to the inner frame by an engagement mechanism that includes at least one tongue and groove attachment and at least one magnetic attachment;
wherein the tongue and groove attachment includes a tongue element comprised by one of the inner frame and the lens assembly, with the tongue element including a longitudinal tongue axis, and a complementary groove element comprised by the other of the inner frame and the lens assembly, with the groove element including a longitudinal groove axis;
where the tongue element is curved along its longitudinal axis to describe a tongue curve, and the groove element is curved along its longitudinal axis to describe a groove curve;
configured such that engagement of each lens assembly with the inner frame describes a top-toward-bottom arced path defined by the groove curve, and disengagement of the lens assembly from the inner frame describes a bottom-toward-top arced path defined by the groove curve.

14. The goggles system of claim 13, where the tongue element comprises at least one longitudinal flange that engages a corresponding at least one longitudinal recess extending long the groove.

15. The goggles system of claim 13, where an intermediate portion of each of said tongue curve and groove curve is nearer a front than a rear of the lens assembly.

16. The goggles system of claim 13, where each lens assembly includes a major curve between left and right ends thereof, and a minor curve between top and bottom borders thereof, with an intermediate portion of said major curve being nearer a front than a rear of the lens assembly.

17. The goggles system of claim 16, where the tongue element is curved along its longitudinal axis to describe a tongue curve, and the groove element is curved along its longitudinal axis to describe a groove curve, and further wherein an intermediate portion of each of said tongue curve and groove curve is nearer a front than a rear of the lens assembly.

18. A goggles system comprising:
an inner frame dimensioned and contoured for positioning against a wearer's face, which inner frame includes at least a first one of a flange-edged tongue or a tongue-receiving groove;
a plurality of interchangeable lens assemblies, wherein:
each lens assembly is removably attachable to the inner frame by an engagement mechanism that includes the other of a flange-edged tongue or a tongue-receiving groove, configured to removably engage with the at least first one of a flange-edged tongue or a tongue-receiving groove, and at least one magnetic attachment structure that corresponds to a magnetically-complementary structure of the inner frame;

each lens assembly includes a major curve between left and right ends thereof, with an intermediate portion of said curve being nearer a front than a rear of the lens assembly; and each of the flange-edged tongue and tongue-receiving groove is complementarily curved along a longitudinal axis of the respective flange-edged tongue and tongue-receiving groove, which respective longitudinal axis is nearer to alignment with an axis between top and bottom borders of the goggles system than a front-rear axis of the goggles system.

19. The goggles device of claim 1, comprising a plurality of complementary magnetic connectors, each of the complementary magnetic connectors including a first portion comprised by the lens assembly and a second portion comprised by the inner frame.

20. The googles device of claim 4, wherein the plurality of inward-facing attachment structures of the lens assembly comprises at least one magnetically-complementing pair including at least a first magnet, a first ferromagnetic mass, or both a first magnet and a first ferromagnetic mass; and at least one of the outward-facing attachment structures includes at least a second magnet, a second ferromagnetic mass, or both a second magnet and a second ferromagnetic mass, where the at least a second magnet, a second ferromagnetic mass, or both a second magnet and a second ferromagnetic mass, aligns with and magnetically attaches to the at least a first magnet a first ferromagnetic mass, or both a first magnet and a first ferromagnetic mass when another of the plurality of inward-facing attachment structures of the lens assembly is engaged with a complementary one of the outward-facing attachment structures, wherein at least one member of each magnetically-complementing pair comprises a magnet.

* * * * *